United States Patent [19]

Selva et al.

[11] Patent Number: 4,607,012

[45] Date of Patent: Aug. 19, 1986

[54] ANTIBIOTIC SB 22484

[75] Inventors: Enrico Selva, Gropello Cairoli; Grazia Beretta; Giorgio Tamoni, both of Milan; Vittorio Arioli, Fino Mornasco; Giovanni Cassani, Pavia; Francesco Parenti, Milan, all of Italy

[73] Assignee: Gruppo Lepetit S.p.A., Italy

[21] Appl. No.: 646,178

[22] Filed: Aug. 30, 1984

[30] Foreign Application Priority Data

Aug. 31, 1983 [GB] United Kingdom ............... 8323382

[51] Int. Cl.$^4$ .................. C12P 7/40; C12P 1/06; C12N 1/20; A61K 35/00
[52] U.S. Cl. ................... 435/136; 435/169; 435/253; 424/115

[58] Field of Search ............... 435/136, 169, 253, 886; 424/115

[56] References Cited

U.S. PATENT DOCUMENTS

4,313,935 2/1982 Komori et al. ............... 435/169

Primary Examiner—Alvin E. Tanenholtz
Attorney, Agent, or Firm—Stephen L. Nesbitt

[57] ABSTRACT

The present invention concerns a new antibiotic substance arbitrarily designated as antibiotic SB 22484, to a process for its production by culturing *Streptomyces sp.* NRRL 15496 or a producing variant or mutant thereof, and to the use of the new antibiotic substance in the treatment of infectious diseases involving microorganisms susceptible to this antibiotic substance.

10 Claims, 3 Drawing Figures

ANTIBIOTIC SB 22484

The present invention concerns a new antibiotic substance arbitrarily designated as antibiotic SB 22484, to a process for its production by culturing Streptomyces sp. NRRL 15496 or a producing variant or mutant thereof, and to the use of the new antibiotic substance in the treatment of infectious diseases involving microorganisms susceptible to this antibiotic substance. Antibiotic SB 22484 possesses an acid function capable of forming salts. The pharmaceutically acceptable salts of antibiotic SB 22484 including the alkali metal, the alkaline-earth metal, the ammonium and the substituted ammonium salts, are part of this invention.

For ease of discussion, when dealing with the biological activity of the compounds of the invention, the term "antibiotic SB 22484" refers to an antibiotic substance selected from antibiotic SB 22484 and its pharmaceutically acceptable salts.

The term "lower alkyl alkanoyl esters" refers to $(C_2-C_6)$alkyl $(C_2-C_6)$alkanoyl esters such as ethyl acetate, propyl acetate, butyl acetate, ethyl propionate, butyl propionate, butyl amylate and the like.

The term "water immiscible lower alkyl ketones" refers to $(C_5-C_{10})$ketones which are scarcely miscible with water such as 2-pentanone, 2-hexanone, 3-hexanone, 2-heptanone, 3-methyl-2-butanone, and 3-methyl-2-pentanone.

The term "halogenated lower hydrocarbons" refers to polyhalogenated $(C_1-C_4)$hydrocarbons such as methylene chloride, chloroform, dichloroethane, and the like.

The term "higher alkanols" refers to straight or branched, linear or cyclic, $(C_4-C_7)$alkanols which are scarcely miscible with water such as butanol, 2-methyl propanol, 2-methyl-2-propanol, pentanol 2-methyl butanol, 2-methyl-2-butanol, cyclohexanol and the like. The antibiotic substance of the invention is characterized by a rather specific antimicrobial spectrum, as in fact it is active on Neisseriae strains, fairly active on Streptococci, Ureaplasma, Mycoplasma, and Hemophilus, while it is almost inactive on Staphylococci and the common gram-negative bacteria such as Proteus, Escherichia and Pseudomonas.

Antibiotic SB 22484 is produced by fermentating a strain which was isolated from a soil sample collected in Italy and which has been deposited on July 6, 1983 with the Internationally recognized collection Agricultural Research Collection (NRRL) located in Peoria, Ill. (USA), under the provisions of the Budapest Treaty. The strain has been accorded the accession number NRRL 15496.

The characteristics of Streptomyces sp. NRRL 15496 are given in the following paragraphs.

MACROSCOPIC AND MICROSCOPIC EXAMINATION

The colonies are characterized by a yellow to a deep chrome yellow vegetative mycelium produced on most of the examined media and a turquoise-green aerial mycelium. The sporophores are arranged in spirals, coils and hooks. The spores are cylindrical with rounded ends and have a diameter of $1.2 \times 2-3$ nm.

Based on the form of the sporophores and on the color of the aerial mycelium, Streptomyces sp. NRRL 15496 has been assigned to the "Group Spira-Green Section", according to the classification of Pridham, Hesseltine and Benedict (T. G. Pridham, C. W. Hesseltine, and R. G. Benedict, "A guide for the classification of Streptomycetes according to selected groups, Appl. Microb. Vol. 6, (1958)).

CULTURAL CHARACTERISTICS

For the examination of the cultural characteristics, Streptomyces sp. NRRL 15496 was cultivated on various standard media suggested by Shirling and Gottlieb (1) with the addition of several media recommended by Wacksman (2).

Color determination was made whenever necessary by the method of Maerz and Paul (3).

All the readings reported in Table I below have been taken after two week incubation at 28° C.

The pH of media used for the classification was approximately neutral (pH 6.6–7).

TABLE I

| Culture medium | CULTURAL CHARACTERISTICS OF STRAIN Streptomyces sp. NRRL 15496 | | |
|---|---|---|---|
| | vegetative mycelium | aerial mycelium | soluble pigment |
| Oat meal agar | abundant growth with thick and wrinkled surface, golden yellow 9/L/6 | yellow aerial mycelium with turquoise green spores | absent |
| Medium ISP No. 2 | abundant growth with wrinkled surface, deep chrome yellow 9L7 | yellow aerial mycelium scarce formation of turquoise green spores | absent |
| Oatmeal agar (medium ISP No. 3) | Abundant growth with smooth surface forsythia yellow 9/K/6 | absent | absent |
| Starch agar (ISP no. 4) | abundant growth with smooth surface, cream | moderate formation of turquoise green spores | absent |
| Glycerol asparagine agar (ISP no. 5) | abundant growth with thick and smooth surface, lemon yellow 9/J/2 | absent | absent |
| Peptone-yeast extract iron agar (medium ISP No. 6) | moderate growth with smooth surface, colorless | absent | absent |
| Tyrosine agar (medium ISP No. 7) | abundant growth with smooth surface, light hazel brown | absent | absent |
| Hickey, and Tresner's agar | abundant growth with wrinkled surface, yellow with green spots 9/I/3 | moderate formation of turquoise green spores | absent |
| Bennett's agar | moderate growth with wrinkled surface, chrome lemon 9/L/3 | absent | |

TABLE I-continued
CULTURAL CHARACTERISTICS OF STRAIN
Streptomyces sp. NRRL 15496

| Culture medium | vegetative mycelium | aerial mycelium | soluble pigment |
| --- | --- | --- | --- |
| Nutrient agar | moderate growth with smooth surface, light cream | absent | absent |
| Potato agar | abundant growth with wrinkled surface, deep chrome 9/6/7 | scarce formation of turquoise green spores | absent |
| Peptone glucose agar | abundant growth, slightly wrinkled, light cream | absent | absent |
| Czapeck glucose agar | abundant growth with wrinkled and crusty surface, yellow 9/I/5 | traces of whitish aerial mycelium | absent |
| Czapeck sucrose agar | scarce growth with thin surface | absent | absent |
| Ca-malate agar | moderate growth with thin surface, canary yellow 10/I/1 | absent | absent |
| Skim milk | abundant growth with wrinkled surface amber | absent | absent |
| Egg albumen | scarce growth, straw | absent | absent |

(1) Shirling E. B., and Gottlieb D., 1966 - Method for characterization of Streptomyces species-Int. J. Syst. Bacteriol, 16, 313–340.
(2) Wacksman, S. A., 1961 - The Actinomycetes - Vol. 2, 328–334. The Williams and Wilkins CO., Baltimore.
(3) Maerz A;, and M. Rea Paul, 1950. A Dictionary of Color, $2^{nd}$ Edition McGraw-Hill Book Company Inc., New York.

UTILIZATION OF CARBON SOURCES

The ability of Streptomyces sp. NRRL 15496 to utilize different carbon sources, which was investigated by the method described by Shirling and Gottlieb, is reported in Table II below:

TABLE II

| Carbon Utilization | |
| --- | --- |
| Carbon Source | Growth |
| Inositol | − |
| Fructose | +++ |
| Rhamnose | +++ |
| Mannitol | +++ |
| Xylose | +++ |
| Raffinose | − |
| Arabinose | ++ |
| Cellulose | − |
| Sucrose | − |
| Mannose | +++ |
| Lactose | +++ |
| Galactose | +++ |
| Salicin | + |
| Dextrose | ++ |

+++ = Strong utilization
++ = Moderate utilization
+ = Weak utilization
− = No utilization

PHYSIOLOGICAL CHARACTERISTICS

Table III reports the physiological characteristics of Streptomyces sp. NRRL 15496.

TABLE III

| Physiological characteristics | |
| --- | --- |
| Tests | Results |
| Starch hydrolysis | +++ |
| H$_2$S formation | + |
| Melanine formation | − |
| Tyrosine hydrolysis | + |
| Casein hydrolysis | ± |
| Calcium malate hydrolysis | − |
| Nitrate reduction | ± |
| Litmus milk | no coagulation no peptonization |
| Gelatin liquefaction | +++ |

− Negative response
+ Weak positive response
++ Positive response
+++ Strong positive response For producing antibiotic SB 22484, a Streptomyces sp. capable of producing it, such as Streptomyces sp. NRRL 15496 or an antibiotic SB 22484 producing variant or mutant thereof, is cultivated under aerobic conditions in an aqueous nutrient medium containing an assimilable source of carbon, an assimilable source of nitrogen and inorganic salts. Said culture medium can be anyone of a number of nutrient media usually employed in the fermentation art, however certain media are preferred. Thus for instance preferred carbon sources are glucose, mannose, galactose, starch, corn meal and the like. Preferred nitrogen sources are ammonia, nitrates, soybean meal, peptone, meat extract, yeast extract, tryptone, aminoacids and the like. Among the inorganic salts which can be incorporated in the culture media are the customary soluble salts capable of yielding sodium, potassium, iron, zinc, cobalt, magnesium, calcium, ammonium, chloride, carbonate, sulfate, phosphate, nitrate and the like ions.

Ordinarily the antibiotic-producing strain is precultured in a shake flask, then the culture is used to inoculate jar fermentors for production of substantial quantities of the antibiotic substances. The medium used for the preculture can be the same as that employed for larger fermentations, but other media can also be employed. The SB 22484 producing strains can be grown at temperatures between about 20° C. and about 40° C. and preferably at temperatures of about 24°–30° C.

During the fermentation, the antibiotic production can be monitored by testing samples of the broth or of extracts of the mycelial cake for antibiotic activity for instance by means of bioassays or TLC or HPLC procedures.

Organisms known to be sensitive to antibiotics SB 22484 are useful for this purpose. Especially useful assay organisms are Neisseria caviae ATCC 14659 and Streptococcus dysgalactiae ATCC 9926. The bioassay is conveniently performed by the agar diffusion method on agar plates. Maximum production of antibiotic activity generally occurs between the second and the fifth day of fermentation.

Antibiotic SB 22484 produced during fermentation of the strain Streptomyces sp. NRRL 15496 is mainly found in the broth. Recovery of said antibiotics is therefore preferably carried out by extraction of the filtered broth. Extraction of the filtered broth is best accomplished with ethyl acetate, but other lower alkyl alkanoyl esters which are immiscible with water, such as methyl acetate, ethyl propionate, and butyl propionate lower hydrocarbons, such as polyhalogenated hydrocarbons such as methylene chloride, dichloroethane and chloroform, lower alkyl ketones such as methyl isopropylketone, methyl isobutylketone, higher alkanols such as butanol, pentanol, and cyclohexanol, and the like may suitably be employed.

Crude antibiotic SB 22484 is then recovered from the extracting solvent by routine procedures which conveniently involve concentration of the extracting solvent to a small volume and precipitation of the crude antibiotic from this solution by the addition of a non-solvent.

Purification of the crude antibiotic substance may then be achieved by means of different techniques such as for instance column chromatography, salt formation or extraction with suitable solvents. When column chromatography is used for the purification, the so-called steric exclusion chromatographic technique is preferably applied for optimum separating results. In particular, Sephadex ®LH-20, (Pharmacia Fine Chemicals, Ab), a controlled pore cross-linked dextran in which most hydroxyl groups have been alkylated, has proved to be an extremely useful stationary phase for excellent purification. Alternatively, the filtered broth is adjusted to pH 5-9 and passed through a non-functionalized polystyrene resin such as Amberlite X-AD-2 (XAD-4, XAD-7, XAD-8) or Diaion HP 20 chromatographic column prepared in deionized water, using a binary mixture 10-90% of acetone, methanol, ethanol, n-propanol, isopropanol or tetrahydrofuran in water as the eluent. The fractions are pooled according to the antibiotic content, concentrated to dryness, brought to pH 4-8 and extracted as described above for the filtration broth.

According to another preferred procedure the filtered broth is adjusted to about pH 7.5 and extracted with a water immiscible lower alkyl alkanoyl ester, and preferably butyl acetate. The organic layer is concentrated and brought to about pH 9.0. This adjustment of the pH is preferably obtained by adding sodium diethylmalonate. The precipitate is taken up with water, adjusted to about pH 4, and extracted again with the selected water immiscible lower alkyl alkanoyl ester. The precipitation with a base, preferably, sodium diethylmalonate, by adjusting the pH to about 9 is repeated to obtain a purified preparation of the antibiotic substance of the invention. Other column chromatographic techniques, such as adsorption chromatography or partition chromatography, may as well be employed for this purification.

Purification by salt formation is simply carried out by dissolving the antibiotic substance in a suitable solvent, and adding an equimolecular amount of a base. The salt which forms is precipitated by adding a non-solvent and is then recovered by filtration. The antibiotic substance in the free acid form may be prepared by dissolving the crude antibiotic in ethyl acetate and then extracting the organic solution with acidic buffers, preferably phosphate buffer at about pH 4.0.

Recovery of the product is then conducted essentially employing common procedures, e.g., by precipitating it from the organic layer or by concentrating the mixture to a small volume. If the product titre is not sufficiently high, it can be further purified by column chromatography applying substantially the same procedure as seen above for the first purification.

When column chromatography is used for the purification, the whole purification procedure can be monitored also by HPLC.

Fractions with similar HPLC profile are combined and concentrated to dryness to give essentially pure antibiotic SB 22484.

Antibiotic SB 22484 thus obtained may be converted into a corresponding non-toxic pharmaceutically acceptable salt. Suitable salts include the alkali and alkaline earth metal salts, typically the sodium, potassium, calcium and magnesium salts, and the ammonium and substituted ammonium salts. Representative substituted ammonium salts include primary, secondary or tertiary ($C_1$-$C_4$)alkylammonium and hydroxy ($C_1$-$C_4$)alkylammonium salts and, according to an embodiment of the present invention, the benzathine, procaine, hydrabamine and similar water insoluble, non-toxic, pharmaceutically acceptable salts. Another preferred class of salts of the compounds of the present invention is represented by the basic addition salts with basic aminoacids such as Arginine or Lysine, or aminosugars such as glucosamine and the like.

The alkali and alkaline earth metal salts are prepared according to the usual procedures commonly employed for preparing metal salts. As an example, antibiotic SB 22484 is dissolved into the minimum amount of a suitable solvent, typically a lower alkanol, the stoichiometric amount of a suitable selected base is gradually added to the obtained solution and the obtained salt is precipitated by the addition of a non-solvent. The alkali or alkaline earth metal salt which forms is then recovered by filtration or evaporation of the solvents.

Alternatively, these salts can be prepared in a substantially anhydrous form through lyophilization; in this case aqueous solutions containing the desired salts, resulting from the salification of antibiotic SB 22484 with a suitably selected alkali or alkaline earth metal carbonate or hydroxide in such a quantity as to obtain a pH comprised between 7.0 and 8.5 are filtered from any insolubles and lyophilized.

The organic ammonium salts can be prepared substantially following the above procedure by adding the properly selected amine to a solution of antibiotic SB 22484 in a suitable solvent and then evaporating off the solvent and the excess of the amine reagent or by lyophilizing the concentrate solution.

PHYSICO-CHEMICAL CHARACTERISTICS OF ANTIBIOTIC SB 22484

Figure 1:
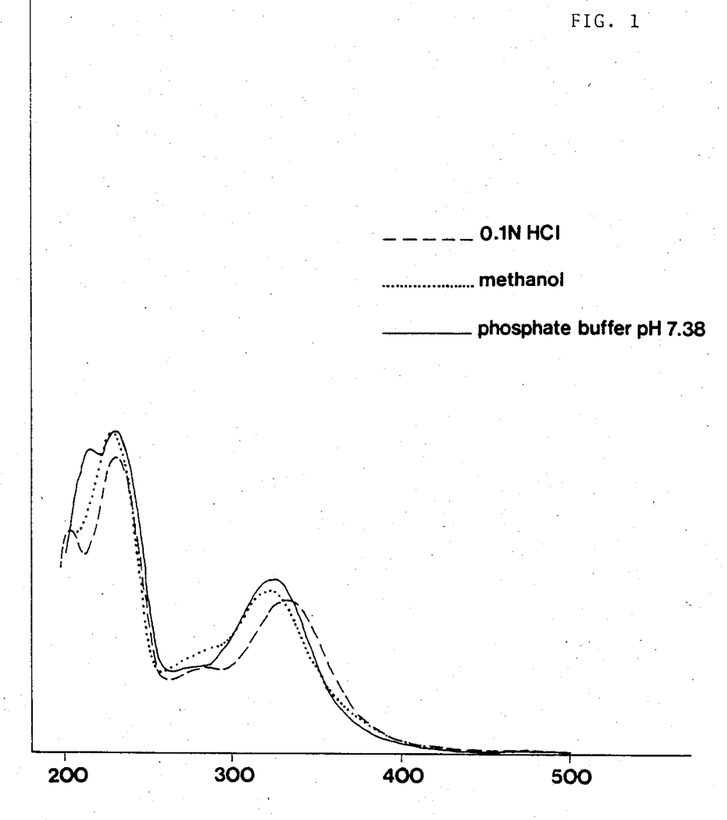

Antibiotic SB 22484 has the following characteristics:
(A) An ultraviolet absorption spectrum, as shown in FIG. 1 of the accompanying drawings, which exhibits the following absorption maxima:

| $\lambda_{max}(nm)$ | $E_{1cm}^{1\%}$ |
| --- | --- |
| (a) in 0.1 NHCl | |
| 230 | 663 |
| 283 | 192 |
| 332 | 343 |
| (b) in phosphate buffer pH 7.38 | |
| 230 | 719 |
| 323 | 391 |
| (c) in 0.1 N sodium hydroxide | |
| 323 | 387 |
| (d) in methanol | |
| 229 | 715 |
| 320 | 365 |

Figure 2:
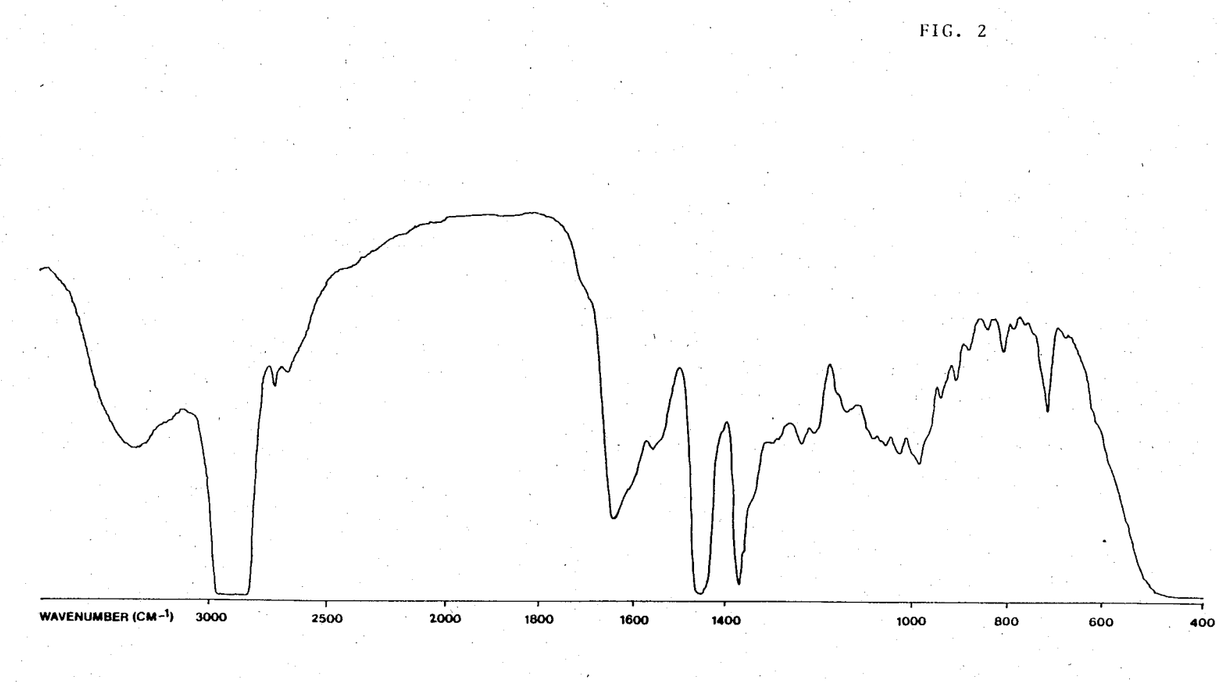
Figure 3:
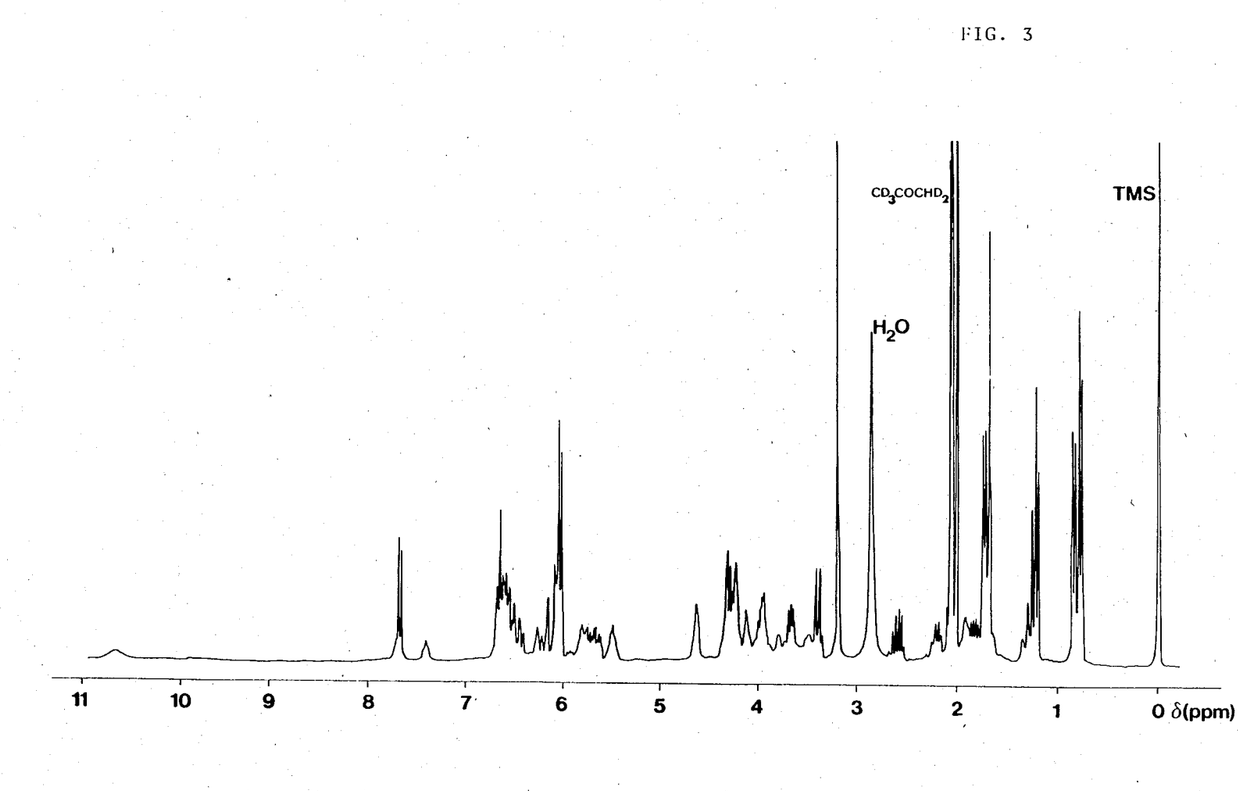

(B) An infrared absorption spectrum which is shown in FIG. 2 of the accompanying drawings and exhibits the following absorption maxima (cm$^{-1}$): 3700–3080, 2980–2840 (nujol); 1645; 1560; 1455 (nujol); 1375 (nujol); 1305; 1240; 1215; 1145; 1090; 1060; 1035; 990; 945; 910; 890; 850; 810; 720 (nujol);

(C) An NMR spectrum which is shown in FIG. 3 and exhibits the following groups of signals (in ppm) in the 270 MHz $^1$H-NMR recorded in hexadeuteroacetone using TMS as the internal reference (0.00 ppm) ($\delta$=ppm): 0.77$\delta$(3H); 0.83$\delta$(3H); 1.21–1.24$\delta$(3H); 1.2–2.7$\delta$(5H); 1.67$\delta$(s, 3H); 1.73$\delta$(3H); 2.01$\delta$(s, 3H); 3.20$\delta$(s, 3H); 3.3–5.6$\delta$(11H); 5.4–6.7$\delta$(13H); 6.04$\delta$(1H); 7.40$\delta$(1H); 7.68$\delta$(1H); 10.53$\delta$(1H). (s=singlet).

(D) A mass spectrum obtained by direct liquid inlet liquid chromatography-mass spectroscophy (LC-MS) using a HP 5985 B apparatus, working in negative ion mode, and conducting the LC at the following conditions:

Column: Brownless Lab. RP 8 10 μm, 25 cm
Flow rate: 1 ml/min
eluent: acetonitrile:0.1M ammonium formate, 60:40
which shows four main peaks having retention times 4.48, 5.03, 5.65 and 7.25 min, respectively, and arbitrarily named Antibiotic SB 22484 factors 1, 2, 3, and 4 respectively;

(E) The following main fragmentation peaks for the above antibiotic factors, namely antibiotic SB 22484 factors 1, 2, 3, and 4:

Factor 1: 752, 734, 716, 684, 538, 598, 566, 500
Factor 2: 766, 748, 730, 698, 652, 612, 580
Factor 3: 752, 734, 716, 684, 638, 598, 566, 500
Factor 4: 766, 748, 730, 698, 652, 612, 580, 500

(F) The following R$_f$ values in various chromatographic systems using silanized silica gel 60 F$_{254}$ Merck plates:

| Elution system (v/v/v) | Rf value |
| --- | --- |
| (1) NaH$_2$PO$_4$/methanol 4/6 | 0.44 |
| | 0.50 |
| | 0.55 |
| (2) NaH$_2$PO$_4$/methanol/acetonitrile 4/5/1 | 0.52 |
| | 0.57 |
| | 0.63 |
| (3) 0.05M Tetrabutylammonium phosphate (pH 7.0): methanol 4/6 | 0.46 |
| | 0.50 |
| | 0.55 |

Visualization: UV light at 254 nm

Antibiotic SB 22484 is an antibacterial agent specifically active against bacterial strains which are responsible for infectuous diseases which are generally difficult to cure such as gonorrhea and meningitis. As already stated, in fact, the antibiotic substance of the invention is active on Neisseriae strains, fairly active on Streptococci, Ureaplasma, Mycoplasma and Hemophylus, while it is almost inactive on Staphylococci and the common gram-negative bacteria such as Proteus, Escherichia and Pseudomonas.

The antibacterial activity of the compounds of the invention can be demonstrated in vitro by means of standard dilution tests.

Iso-Sensitest broth (Oxoid) and Todd-Hewitt broth (Difco) are used for staphylococci and streptococci, respectively, Neisseriae strains are cultured on GC agar base (Difco)+1% Iso-Vitalex (BBL) and Hemophylus is cultured on GC agar base (Difco)+1% Iso-Vitalex (BBL)+1% hemoglobin (Difco). Broth cultures are diluted so that the final inoculum is about 10$^4$–10$^5$ colony forming units/ml (CFU/ml). Minimal inhibitory concentration of (MIC) is considered as the lowest concentration antibiotic which shows no visible growth after 18–24 h incubation at 37° C. Neisseriae strains are incubated in a CO$_2$ enriched atmosphere.

The in vitro activity spectra of antibiotic SB 22484 is summarized in the following table:

TABLE IV

| In vitro antibacterial activity of antibiotic SB 22484 | |
| --- | --- |
| Strain | M.I.C. (μg/ml) |
| S. pyogenes C 203 SKF 13400 | 8 |
| S. dysgalactiae ATCC 9926 | 8 |
| S. pneumoniae UC 41 L 44 | 4 |
| H. influenzae type b ATCC 9795 | 32 |
| H. influenzae type d ATCC 9332 | 32 |
| H. influenzae L 990(*) | 32 |
| M. gallisepticum 9/6 Weybridge L 431 | 4 |
| N. caviae ATCC 14659 | 0.5 |
| N. gonorrhoeae NCTC 8254 | 0.5 |
| N. gonorrhoeae L 997(*) | 2 |
| N. gonorrhoeae (*)L 1596(**) | 2 |
| N. gonorrhoeae (*)L 1599(***) | 1 |
| N. meningitis A ATCC 13077 | 4 |
| N. meningitis B ATCC 13090 | 1 |
| N. meningitis C ATCC 13102 | 2 |
| N. meningitis D ATCC 13113 | 1 |
| N. meningitis ATCC 13804 | 1 |

L numbers identify applicant internal collection numbers.
(*)Clinically isolated strains which are identified by the applicants' internal collection number.
(**)Clinically isolated strain resistant to spectinomycin (MIC > 128 under these conditions)
(***)Clinically isolated β-penicillinase producing strain (resistant to penicillin with a MIC > 50 under these conditions)

The activity on Ureaplasma urealyticum was assayed after growth of the microorganism on a medium of the following composition:

| | |
| --- | --- |
| PPLO broth without crystal violet (Difco) | 80 ml |
| 1 N HCl | 0.9 ml |
| Horse serum (Sclavo) | 10 ml |
| 5% Urea (C. Erba RP) | 1 ml |
| 0.2% Phenol red | 1 ml |
| adjusted at about pH 6. | |

The minimal inhibitory concentration (MIC) was determined in tubes by the two-fold serial dilution method (range of concentrations, 0.008 to 128 μg/ml).

Volumes of 1 ml per tube, inoculated with 10$^2$–10$^3$ colour changing units (ccu) from 20–24 h broth-cultures, were used. The tubes were incubated at 37° C.

MIC end point was taken as the lowest concentration of antibiotic which prevented a colour change, evaluated at a time when the control culture showed a colour change corresponding to pH 7.8 (determined by a comparison of the colour of the medium with the colour of the same medium adjusted to various pH values). This change occurred after about 24 h of incubation when inocula of approximately $10^2$–$10^3$ ccu/ml were used.

The inoculum size was estimated as follows: serial 10-fold dilutions of the broth cultures used as inoculum were added to broth; ccu/ml were calculated on the basis of the lowest dilution which showed a colour change.

The results of this test on a clinically isolated strain are reported below:

|  | MIC (µg/ml) |
|---|---|
| U. urealyticum L 1479 | 8 |

In bactericidal "in vitro" experiments the antibiotic SB 22484 kills 99.9% of cells of N. gonorrhea L 997, in logarithmic phase of growth on GC agar base (Difco)+1% Iso-Vitalex (BBL), after incubation for 24 h at 37° C. with a concentration corresponding to 5 times the MIC (10 µg/ml).

Preliminary results of in vivo tests show that antibiotic SB 22484, when given s.c. 200 mg/kg to mice experimentally infected with S. pyrogenes according to V. Arioli et al., J. Antibiotics 29, 511, (1976), protects 3 out of 5 animals. Moreover the compounds of the present invention show a very low toxicity since their $LD_{50}$ in intraperitoneally administered mice is higher than 1000 mg/kg (highest dose tested).

In view of their antimicrobial activity the compounds of the invention can effectively be employed as the active ingredients of antimicrobial preparations used in human and veterinary medicine either for the prevention or the therapy of infectious diseases caused by susceptible pathogenic bacteria.

In view of the antimicrobial activities of antibiotic SB 22484 as well as the corresponding salts, they can be used in pharmaceutical or veterinary formulations. More particularly, antibiotic SB 22484 and the corresponding non-toxic pharmaceutically acceptable salts can be used in mixtures of any proportion.

As shown above antibiotic SB is a complex of at least four major components (SB 22484 factor 1, 2, 3 and 4). As it is apparent to the man skilled in the art, the percentages of these factors in the complex can vary even from batch to batch depending on various parameters such as culture media and fermentation conditions and routine variations in the isolation and purification process. The present disclosure therefore encompasses all the mixtures of antibiotic SB 22484 factors 1, 2, 3, and 4 in any proportions. These mixtures are generally intended to be encompassed by the expression "antibiotic SB 22484".

In view of its antimicrobial activity, antibiotic SB 22484 may find application as an antimicrobial agent of primary choice in the treatment of gonorrhea. Gonorrhea is presently being treated with a number of different antibiotics, primarily with penicillin and spectinomycin and alternatively with tetracycline or ampicillin. However, as the incidence of gonorrhea has risen steadily in the last 15-20 years, the widespread use of these antibiotics for treatment of gonorrhea has resulted in an increasing frequency of drug resistance. Because of this, the development of new antibacterial compounds which are remarkably active against the microorganism responsible for gonorrhea, including also some resistant to drugs in current therapy, represents an advance in the treatment of this disease.

In general, for antibacterial treatment antibiotic SB 22484 as well as its non-toxic pharmaceutically acceptable salts can be administered by different routes such as topically or parenterally. However, the parenteral administration is the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water for injection, is added thereto.

Depending on the route of administration, these compounds can be formulated into various dosage forms.

In some instances, it could be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., USA, page 1614).

This could be especially the case when it is desired the the antimicrobial be particularly active or adsorbed in the enteric tract, while passing unaltered through the gastric tract.

The amount of active principle to be administered depends on various factors such as the size and condition of the subject to be treated, the route and frequency of administration, and the causative agent involved. The antibiotic substance of the present invention, namely antibiotic SB 22484 and the physiologically acceptable salts thereof, are generally effective at a daily dosage comprised between about 5 and about 100 mg of active ingredient per Kg of patient body weight, optionally divided in 2 to 4 administrations per day.

Particularly desirable compositions are those prepared in dosage units containing from about 100 to about 5,000 mg per unit.

However, when used for the treatment of gonorrhea, where because of practical problems a single dose therapy is highly preferred, higher minimum doses of antibiotic SB 22484 generally ranging between 10 and 100 mg/Kg, should be employed, in order to maintain an effective blood level of the drug over an extended period of time.

Furthermore, in the treatment of gonorrhea, a sustained-action parenteral dosage form is preferably employed. Sustained-action formulations can be prepared based on different mechanisms and methods, as known in the art. A preferred method for preparing a sustained-action formulation containing antibiotic SB 22484 involves the use of a water insoluble salt of this antibiotic substance such as the benzathine, procaine, hydrabamine and the like salts, suspended in an aqueous or oily medium.

These salts in fact, upon intramuscular injection, are released very slowly because of low water-solubility thus giving substained blood levels of the antibiotic substance.

Preparation of pharmaceutical compositions:

A unit dosage form for intramuscular injection is prepared with 2000 mg of the procaine salt of antibiotic SB 22484 suspended in 3 ml of refined peanut oil gelled with 2% aluminum stearate.

A unit dosage form for intramuscular injection is prepared with 250 mg of antibiotic SB 22484 dissolved in 5 ml of a solvent having the following composition: propyleneglycol 40%, ethanol 10%, 0,5% trihydroxymethylamine (w/v), 50%.

A unit dosage form for intramuscular injection is prepared with 5 ml of sterile suspension USP containing 8% propylene glycol and 3500 mg of antibiotic SB 22484.

A unit dosage form for intramuscular injection is prepared with 2000 mg of antibiotic SB 22484 sodium salt suspended in 5 ml of sterile water for injection.

The following examples are provided to further illustrate the invention, but they should not be construed as limiting its scope.

EXAMPLE 1

Production of the antibiotic substance

A lyophilized tube containing a culture of Streptomyces Sp. NRRL 15496 is open and aseptically transferred into a slant of oatmeal agar. After 10 day incubation at about 28° C. the slant culture is suspended in distilled water and inoculated into a baffled 500-ml Erlenmeyer flask containing 100 ml of medium having the following composition:

| Beef extract | 5 g |
| --- | --- |
| Peptone | 5 g |
| Enzymatic casein hydrolizate | 3 g |
| Yeast extract | 5 g |
| NaCl | 1.5 g |
| Dextrose | 20 g |
| Distilled water | 1.000 ml |

This flask is incubated at 28° C., 220 rpm for about 48 hours.

The entire culture is used to inoculate a 10 l fermentor containing 6 l of fermentation medium having the following composition:

| Beef extract | 4 g |
| --- | --- |
| Peptone | 4 g |
| NaCl | 2.5 g |
| Yeast extract | 1 g |
| Soybean meal | 10 g |
| Dextrose | 25 g |
| CaCO$_3$ | 5 g |
| Tap water | 1000 ml |

This fermenter is incubated at 28° C., 900 rpm, with an aeration flow of 1 v/v/m.

Maximum antibiotic activity is obtained after about 40 hours of fermentation.

The antibiotic level is determined with the paper-disk agar assay method using Neisseria caviae ATCC 14659 and Streptococcus dysgalactiae ATCC 9926 as test organisms.

EXAMPLE 2

Massive production of the antibiotic substance

A lyophilized tube containing a culture of Streptomyces Sp. NRRL 15496 is open and aseptically transferred onto a slant of oatmeal agar. After 10 day incubation at 28° C., the slant culture is suspended in distilled water and inoculated into 2 baffled 2000-ml Erlenmeyer flasks containing 500 ml of medium having the following composition:

| Beef extract | 5 g |
| --- | --- |
| Peptone | 5 g |
| Enzymatic casein hydrolizate | 3 g |
| Yeast extract | 5 g |
| NaCl | 1.5 g |
| Dextrose | 20 g |
| Distilled water | 1000 ml |

These 2 flasks are incubated at 28° C., 220 rpm, for about 40 hours.

The culture of the two flasks is used to inoculate a 50 l fermentor containing 30 l of seed medium having the following composition:

| Beef extract | 4 g |
| --- | --- |
| Peptone | 4 g |
| NaCl | 2.5 g |
| Yeast extract | 1 g |
| Soybean meal | 10 g |
| Dextrose | 25 g |
| CaCO$_3$ | 5 g |
| Tap water | 1000 ml | and fermented at 28° C., 500 rpm, with an aeration flow of 1 v/v/m.

After 24 hours of fermentation, the 30 liters of seed culture are inoculated into a 300-l fermentor containing 200 l of medium having the same percent composition as the preceeding one. This fermenter is incubated at a temperature of 28° C., 240 rpm, with an aeration flow of 1 v/v/m.

Maximum antibiotic activity is obtained after about 40 hours of fermentation.

The antibiotic level is determined with the "paper-disc agar assay method" using Neisseria caviae ATCC 14659 grown overnight in brain heart agar medium at 37° C., as test organism. The broth gives an inhibition zone with a diameter of 23 mm on a 10 mm paper disk.

EXAMPLE 3

Isolation and purification of antibiotic SB 22484

The fermentation broth (60 l) is filtered in the presence of the filter-aid Clarcel ®-flow-ma and the filtrate is adjusted to about pH 7.0 and extracted with ethyl acetate (about 60 ml). The organic phase is separated by centrifugation and concentrated to a small volume. Petroleum ether is then added to the oily residue and the crude antibiotic precipitate is collected by filtration. A fraction of this material (4.5 g) is dissolved in methanol (50 ml), applied to a chromatographic column (1 m) containing 1,5 ml of Sephadex L 20 in methanol, and the system is eluted with the same solvent. Fractions of about 20 ml are collected and assayed by paper-disc diffusion assay against N. caviae ATCC 14659 and by TLC and HPLC analysis.

The antibiotic containing fractions are pooled and concentrated to dryness. The oily residue is dissolved in a minimum amount of tetrahydrofuran, ethyl ether is added thereto and the mixture is shaken for a suitable time until a precipitate forms which is collected and dried to yield about 960 mg of a pure preparation of antibiotic SB 22484 having the physico-chemical characteristics described above.

We claim:

1. Antibiotic SB 22484 or a pharmaceutically acceptable salt thereof, having, in the form of the free acid, the following characteristics:

(A) An ultraviolet absorption spectrum, which exhibits the following absorption maxima:

| $\lambda_{max(nm)}$ | $E_{1cm}^{1\%}$ |
|---|---|
| (a) in 0.1 NHCl | |
| 230 | 663 |
| 283 | 192 |
| 332 | 343 |
| (b) in phosphate buffer pH 7.38 | |
| 230 | 719 |
| 323 | 391 |
| (c) in 0.1 N sodium hydroxide | |
| 323 | 387 |
| (d) in methanol | |
| 229 | 715 |
| 320 | 365 |

(B) An infrared absorption spectrum which exhibits the following absorption maxima ($cm^{-1}$): 3700–3080, 2980–2840 (nujol); 1645; 1560; 1455 (nujol); 1375 (nujol); 1305; 1240; 1215; 1145; 1090; 1060; 1035; 990; 945; 910; 890; 850; 810; 720 (nujol);

(C) A NMR spectrum which as the following groups of signals (in ppm) in the 270 MHz $^1$H-NMR recorded in hexadeuteroacetone using TMS as the internal reference (0.00 ppm) ($\delta$=ppm): 0.77$\delta$(3H); 0.83$\delta$(3H); 1.21–1.24$\delta$(3H); 1.2–2.7$\delta$(5H); 1.67$\delta$(s, 3H); 1.73$\delta$(3H); 2.01$\delta$(s, 3H); 3.20$\delta$(s, 3H); 3.3–5.6$\delta$(11H); 5.4–6.7$\delta$(13H); 6.04$\delta$(1H); 7.40$\delta$(1H); 7.68$\delta$(1H); 10.53$\delta$(1H); (s=singlet);

(D) A mass spectrum obtained by direct liquid inlet LC-MS using a HP 5985 B apparatus, working in negative ion mode and conducting the LC under the following conditions:
Column: Brownlee Lab. RP 8 10 μm, 25 cm (an octylsilane functionalized silica gel)
Flow rate: 1 ml/min
eluent: acetonitrile:0.1M ammonium formate=60:40
which shows four main peaks having retention times 4.48, 5.03, 5.65 and 7.25 min, respectively. They are arbitrarily named antibiotic SB 22484 factors 1, 2, 3, and 4 respectively;

(E) The following main fragmentation peaks for the above identified antibiotic factors, namely antibiotic SB 22484 factors 1, 2, 3 and 4:
Factor 1: 752, 734, 716, 684, 538, 598, 566, 500
Factor 2: 766, 748, 730, 698, 652, 612, 580
Factor 3: 752, 734, 716, 684, 638, 598, 566, 500
Factor 4: 766, 748, 730, 698, 652, 612, 580, 500

(F) The following Rf values in various chromatographic systems using silanized silica gel 60 $F_{254}$ Merck plates:

| Elution system (v/v/v) | Rf value |
|---|---|
| (1) NaH$_2$PO$_4$/methanol 4/6 | 0.44 |
| | 0.50 |
| | 0.55 |
| (2) NaH$_2$PO$_4$/methanol/acetonitrile 4/5/1 | 0.52 |
| | 0.57 |
| | 0.63 |
| (3) 0.05M Tetrabutylammonium phosphate (pH 7.0): methanol 4/6 | 0.46 |
| | 0.50 |
| | 0.55 |

Visualization: UV light at 254 nm.

2. Antibiotic SB 22484 as a mixture essentially containing its four main components SB 22484 factors 1, 2, 3, and 4 in any proportion.

3. A process for producing antibiotic SB 22484 or a pharmaceutically acceptable salt thereof which comprises cultivating a Streptomyces sp. NRRL 15496 or an antibiotic SB 22484 producing variant or mutant thereof, under submerged aerobic conditions in the presence of assimilable sources of carbon, nitrogen and inorganic salts, recovering and isolating said antibiotic from the fermentation broths, and transforming it into the desired salt, if required.

4. A process according to claim 3 wherein the cultivation of the producing strain is carried out at a temperature between 20° C. and 40° C.

5. A process to claim 3 wherein the recovery of the antibiotic substance is conducted by extracting the filtered fermentation broth with a solvent selected from water immiscible lower alkyl alkanoyl acid esters, lower polyhalogenated hydrocarbons, and higher alkanols.

6. A process according to claim 2 wherein the isolation of the antibiotic substance is obtained by steric exclusion column chromatography on derivatized controlled pore cross-linked dextran or non-functionalized polystyrene.

7. A process in claim 6 wherein the chromatography column is eluted with a binary mixture 10% to 90% of acetone, methanol, ethanol, n-propanol, isopropanol or tetrahydrofuran in water.

8. A process as in claim 3 wherein the recovery of the antibiotic substance is obtained by adjusting the pH of the fermentation broth to about 7.5, extracting it with a water-immiscible lower alkyl alkanoyl ester, bringing the pH to about 9.0, recovering by filtration and taking up with water the precipitate which forms, adjusting this suspension to about pH 4, extracting with a water immiscible lower alkanoyl ester, and again precipitating by bringing the pH to about 9.

9. A biologically pure culture of Streptomyces sp. NRRL 15496 or a variant thereof.

10. A biologically pure culture of Streptomyces sp. NRRL 15496 or a mutant or variant thereof which is capable of producing antibiotic SB 22484 when submitted to aerobic fermentation conditions in the presence of assimilable sources of carbon, nitrogen, and inorganic salts.

* * * * *